(12) United States Patent
Liao

(10) Patent No.: US 7,033,329 B2
(45) Date of Patent: Apr. 25, 2006

(54) HUMAN BODY MASSAGER WITH MAGNETIC FIELD GENERATOR

(76) Inventor: Lu-Jung Liao, No. 19-23, Kuang Min Road., Si Tun Area, Taichung (TW)

(*) Notice: Subject to any disclaimer, the term of this patent is extended or adjusted under 35 U.S.C. 154(b) by 132 days.

(21) Appl. No.: 10/282,042

(22) Filed: Oct. 29, 2002

(65) Prior Publication Data

US 2004/0006289 A1    Jan. 8, 2004

(30) Foreign Application Priority Data

Jul. 2, 2002    (TW) .............................. 91209995 U

(51) Int. Cl.
  *A61H 35/00* (2006.01)
  *A61H 33/00* (2006.01)
  *A61H 33/04* (2006.01)
(52) U.S. Cl. ................... 601/15; 601/17; 601/22; 601/27; 601/158; 600/13
(58) Field of Classification Search ............... None
See application file for complete search history.

(56) References Cited

U.S. PATENT DOCUMENTS

| | | | | |
|---|---|---|---|---|
| 1,618,165 | A | * | 2/1927 | Boschelli ................. 601/136 |
| 2,604,091 | A | * | 7/1952 | Hansen ..................... 601/63 |
| 3,043,294 | A | * | 7/1962 | Neff .......................... 601/61 |
| 4,850,340 | A | * | 7/1989 | Onishi ....................... 601/18 |
| 5,080,091 | A | * | 1/1992 | Peterson et al. ........... 601/168 |
| 5,527,259 | A | * | 6/1996 | Grace et al. ................ 600/14 |
| 5,588,161 | A | * | 12/1996 | Barradas ..................... 4/662 |
| 5,693,004 | A | * | 12/1997 | Carlson et al. ............. 601/23 |
| 5,741,317 | A | * | 4/1998 | Ostrow ....................... 607/85 |
| 6,461,377 | B1 | * | 10/2002 | An .............................. 601/15 |
| 6,500,110 | B1 | * | 12/2002 | Davey et al. ............... 600/13 |
| 2002/0056158 | A1 | * | 5/2002 | Ferber et al. ................ 4/622 |

\* cited by examiner

*Primary Examiner*—Danton DeMille
(74) *Attorney, Agent, or Firm*—Bacon & Thomas, PLLC

(57) ABSTRACT

A human body massager is constructed to include a base, the base having a supporting portion adapted for supporting a part of the user's body, and a magnetic field generator installed in the base and adapted for generating a variable magnetic field involved with the part of the user's body supported on the supporting portion.

24 Claims, 14 Drawing Sheets

HUMAN BODY MASSAGER WITH MAGNETIC FIELD GENERATOR

BACKGROUND OF THE INVENTION

1. Field of the Invention

The present invention relates to a massager and, more particularly, to a human body massager that uses a magnetic field to massage a particular part of the body.

2. Description of the Related Art

There is known a magnetic massaging apparatus that uses magnetic field induction to stimulate the circulation of blood. This structure of magnetic massaging apparatus comprises a support made in the form of a seat or bed for supporting the user's body, and magnetic field generating means arranged in the support for producing a magnetic induction to stimulate the circulation of blood of the user. This massaging apparatus is less effective because the phase and intensity of the magnetic filed generated by the magnetic field generating means is not variable.

There are known mechanical massaging apparatus that, when started, move movable members to rub and knead the muscles and joints or to vibrate the user's body, achieving a massaging effect. These mechanical massaging apparatus include massaging chairs, massaging bars, foot massagers, and vibration type blood circulation massagers. However, the use of a mechanical massaging apparatus may cause hurt to the human body due to poor mechanical design, unstable output, wrong posture of the user, or improper use of the apparatus.

There are also known foot spa apparatus for massaging the user's feet with hot water. These foot spa apparatus commonly comprises a base, a plastic shell supported on the base and adapted to carrying a liquid in which the user can dip the feet, a water heater and an air bubble generator installed in the receiving chamber defined within the shell and the base. The water heater comprises a water passage for circulation of the liquid carried in the shell, a pump adapted to pump the liquid through the water passage, and an electric heating element adapted to heat the liquid passing through the water passage. The air bubble generator comprises an air pump and an air tube connected between the air pump and a hole in the shell to guide air from the air pump into the liquid in the shell. When in use, the water heater pumps and heats the liquid carried in the shell, and the air bubble generator pumps air into the liquid in the shell to produce bubbles. These foot spa apparatus are functional, however the massaging effect of relaxing the muscles is still improvable.

SUMMARY OF THE INVENTION

The present invention has been accomplished under the circumstances in view. It is one object of the present invention is to provide a human body massager, which effectively stimulates the circulation of blood of the user. To achieve this object, the human body massager comprises a base, the base having a supporting portion adapted for carrying a part of the user's body, and a magnetic field generator installed in the base and adapted for generating a variable magnetic field to stimulate the circulation of blood of the part of the user's body supported on the supporting portion. It is another object of the present invention to provide a human body massager, which effectively relaxes the muscles of the body of the user without causing hurt to the user's body. To achieve this object, the human body massager comprises a base, the base having a recessed receiving chamber in the top for carrying a liquid in which a part of the user's body is rested, a plurality of magnetic massaging elements put in the liquid in the recessed receiving chamber, and a magnetic field generator installed in the base and adapted for generating a variable magnetic field to the recessed receiving chamber to force the magnetic massaging elements to move in the liquid in the recessed receiving chamber, so as to massage the dipped part of the user's body and to relax the muscles of the dipped part of the user's body.

DETAILED DESCRIPTION OF THE PREFERRED EMBODIMENT

Figure 1:
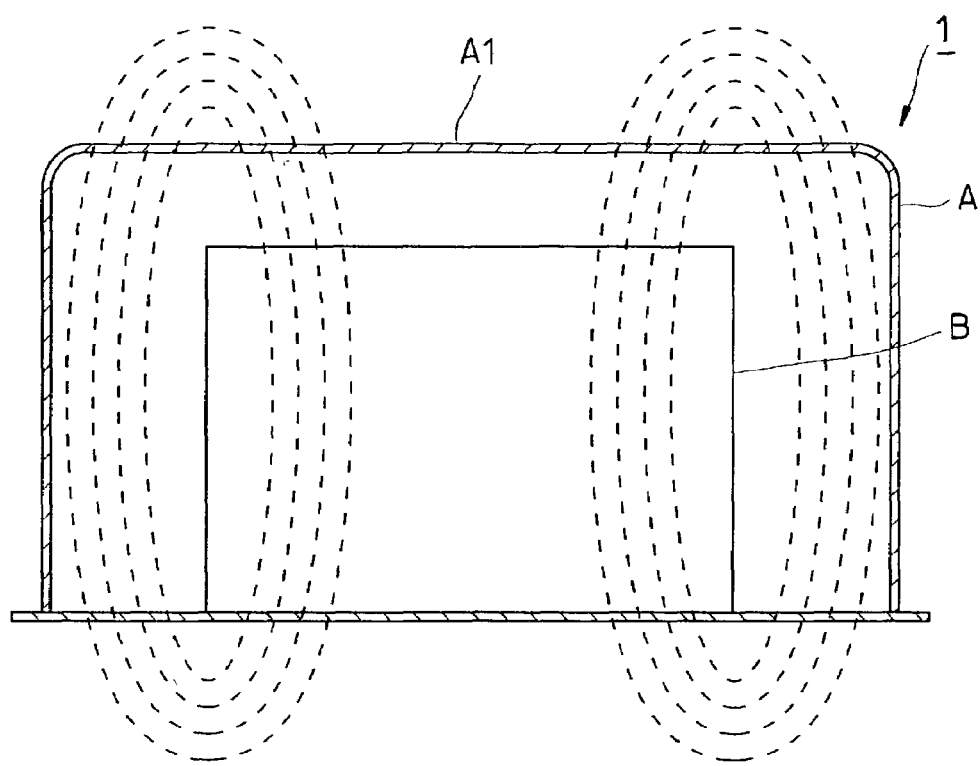
FIG. 1 is a schematic drawing showing the main architecture of the present invention.

Referring to FIG. 1 a human body massager 1 is shown comprising a base A, the base A having supporting portion A1, and a magnetic field generator B mounted in the base A and controlled to produce a variable magnetic field around the supporting portion A1.

The supporting portion A1 is adapted to support a part or the whole of the body of the user, or supporting/carrier means for supporting/carrying or even massaging a part of the whole of the body of the user.

The aforesaid variable magnetic field means the phase or intensity of the magnetic field changes with time in a particular position within the inductive range of the magnetic field. The magnetic field generator B is installed in the base A, and controlled to provide the supporting portion A1 with said variable magnetic field.

By means of the aforesaid arrangement, the part or whole of the body of the user supporting/carrying on the supporting portion A1 receives the radiation of the magnetic field, achieving a massaging effect. Because the magnetic field is variable, a better massaging effect is achieved.

Figure 2:
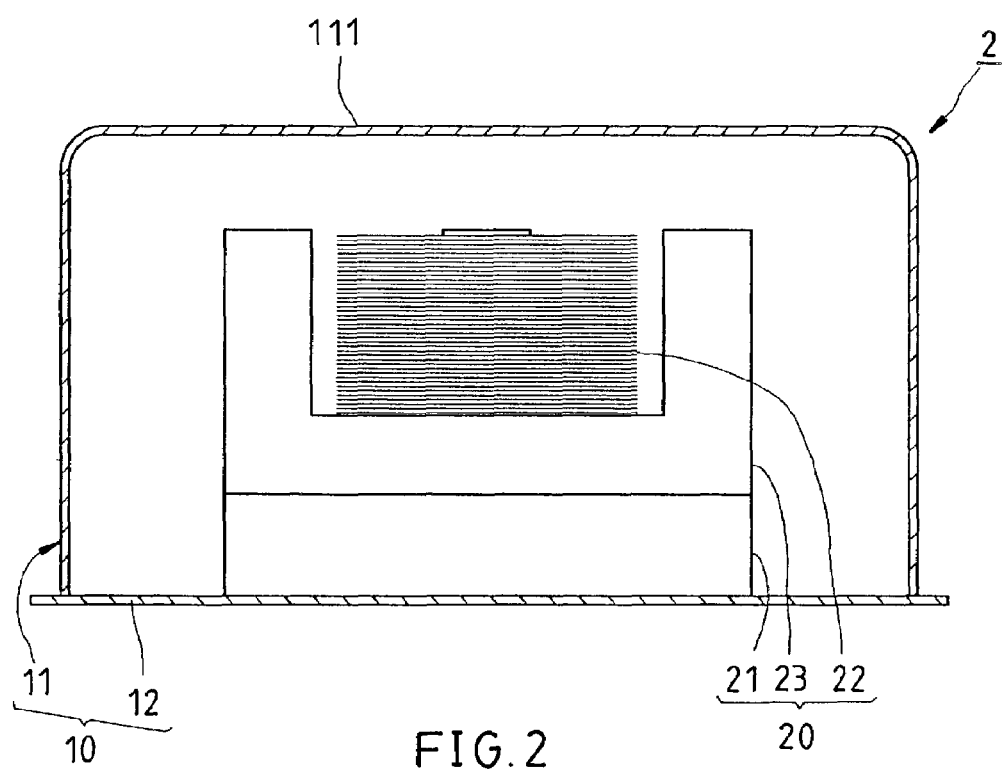
FIG. 2 is a sectional view of a human body massager according to the first embodiment of the present invention.

The invention will now be described by way of examples. FIG. 2 shows a human body massager 2 according to the first embodiment of the present invention. According to this embodiment, the human body massager 2 comprises a base 10 and a magnetic field generator 20. The base 10 comprises a hollow shell 11 injection-molded from plastics. The shell 11 has a flat top panel, forming a supporting portion 111 for supporting/carrying a part of the body of the user, for example, the arm, the leg, or the hips. The shell 11 defines a receiving chamber having a bottom opening. The base 10 further comprises flat a cover plate 12 fixedly fastened to the hollow shell 11 by screws to close the bottom opening of the shell 11. The magnetic generator 20 is comprised of an electric current controller 21, a stack of steel plates 23, and a winding 22 wound round the stack of steel plates 23. The electric current controller 21 produces an electric current that changes the intensity with time. The output current of the electric current controller 21 is sent to the winding 22, thereby causing the stack of steel plates 23 to produce a magnetic field that changes the intensity with time. The magnetic field generator 20 is mounted on the cover plate 12 inside the shell 11. The inductive range of the generated magnetic field covers the supporting portion 111. In general, the magnetic field generator 20 provides the supporting portion 111 with a magnetic field that changes its intensity with time.

Figure 3:
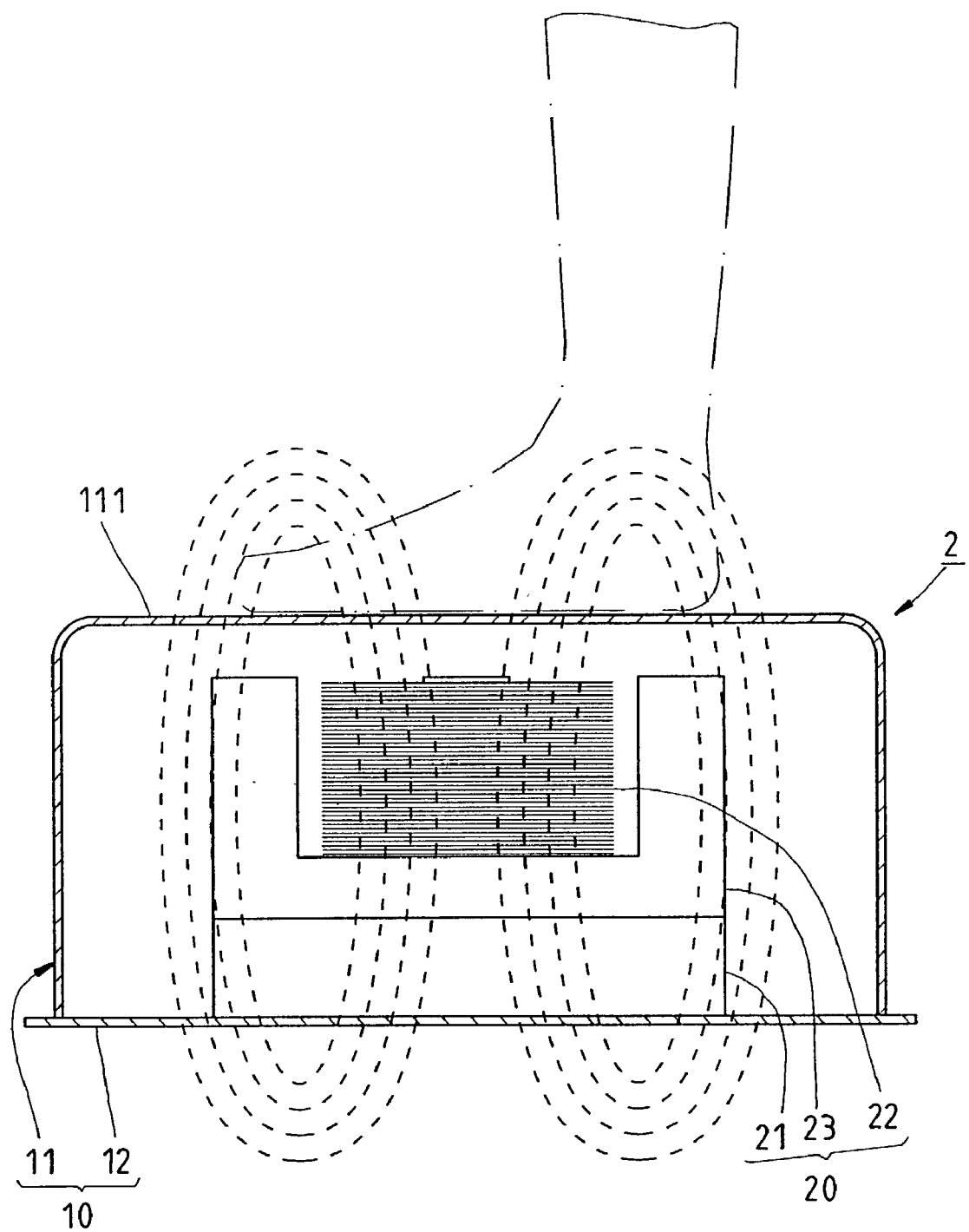
FIG. 3 is a schematic drawing showing an application example of the human body massager according to the first embodiment of the present invention.

Referring to FIG. 3, when the user put a part of the body, for example, the foot on the supporting portion 111, the magnetic field generator 20 is started to produce a magnetic field that changes the intensity with time, and stimulates the flood circulation of the foot, achieving a massaging effect.

The current controller 21 produces an electric current that changes the intensity with time. By means of changing the circuit design, the current controller 21 can be made to produce an electric current that changes the direction with time, causing the stack of steel plates 23 to produce a magnetic field that changes the intensity and phase with time. This design achieves a better massaging effect.

Figure 4:
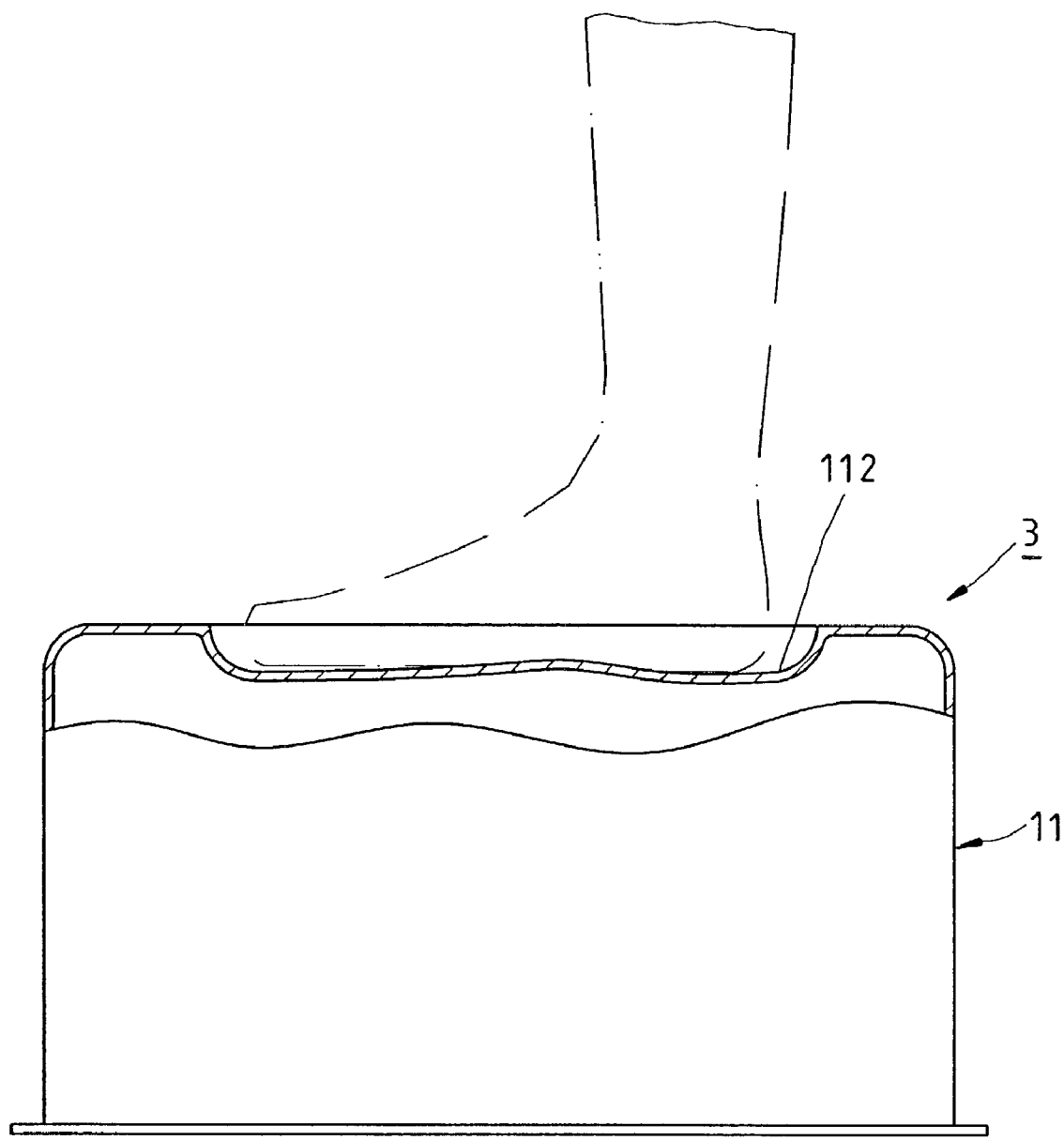
FIG. 4 is schematic sectional view of a human body massager according to the second embodiment of the present invention.

FIG. 4 shows a human body massager 3 according to the second embodiment of the present invention. According to this embodiment, the supporting portion 111 is a recessed member formed integral with the top panel of the hollow shell 11 of the human body massager 3. The recessed supporting portion 111 fits the shape of a particular part, for example, the foot, palm, or hips of the body.

Figure 5:
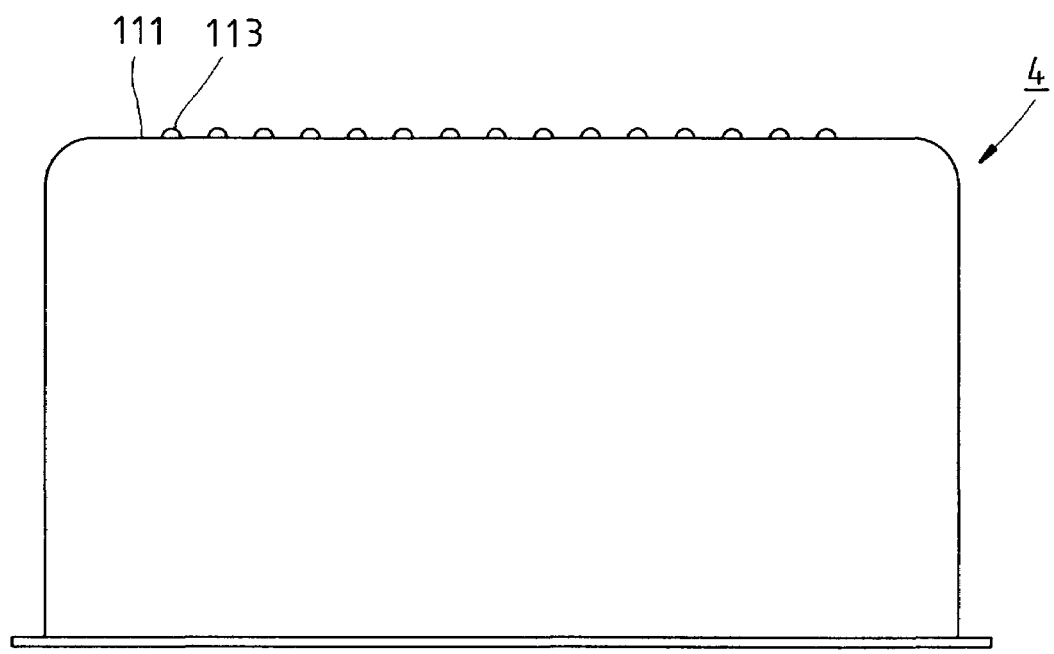
FIG. 5 is a side plain view of a human body massager according to the third embodiment of the present invention.
Figure 6:
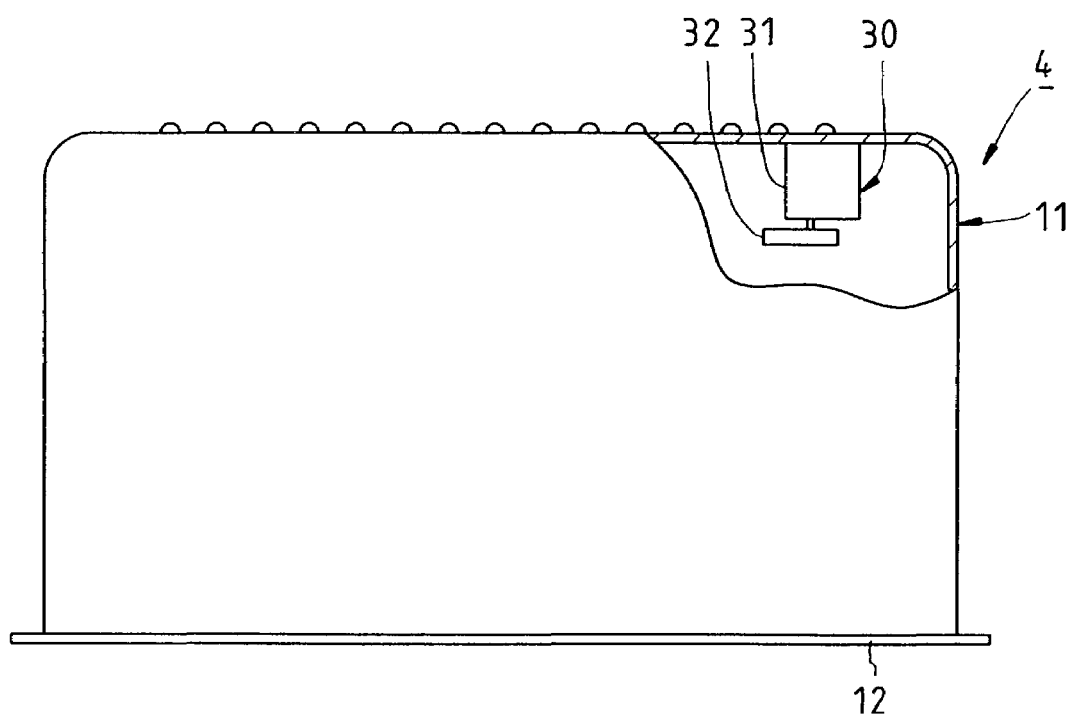
FIG. 6 is a side plain view, partially in section, of the human body massager according to the third embodiment of the present invention.

FIGS. 5 and 6 show a human body massager 4 according to the third embodiment of the present invention. According to this embodiment, the supporting portion 111 of the human body massager 4 has raised portions 113 for massaging a particular part, for example, the foot, palm, or hips of the body. Further, a vibrator 30 is installed in the shell 11 (or alternatively in the cover plate 12) to vibrate the shell 11 when massaging. According to this embodiment, the vibrator 30 comprises a motor 31, and an eccentric wheel 32 connected to the output shaft of the motor 31.

Figure 7:
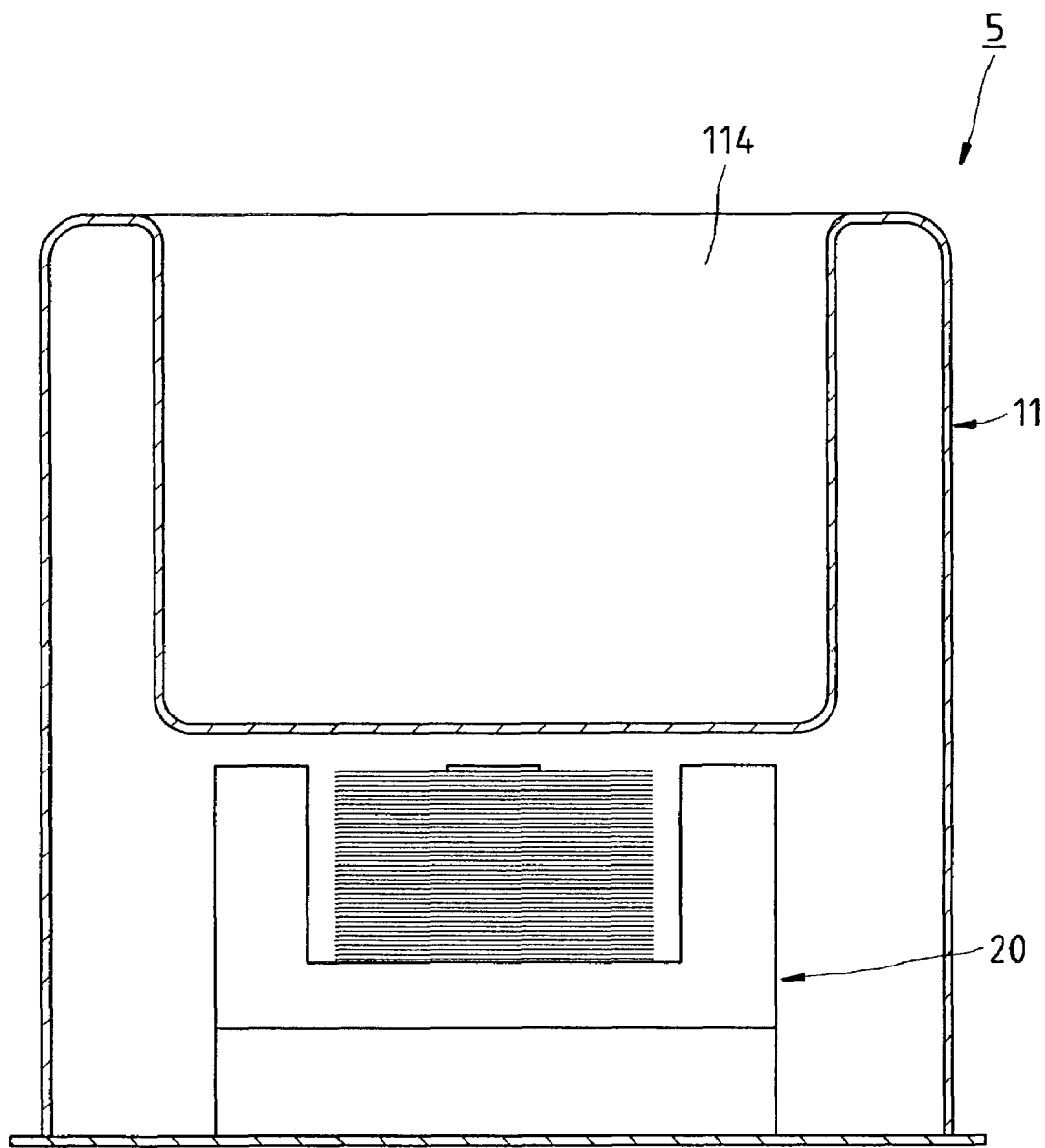
FIG. 7 is a sectional view of a human body massager according to the fourth embodiment of the present invention.

FIG. 7 shows a human body massager 5 according to the fourth embodiment of the present invention. According to this embodiment, the supporting portion 114 of the human body massager 5 is a recessed receiving chamber formed in the top side of the shell 11 for holding a liquid, for example, hot water or medical care solution. When in use, the user can dip the hands or feet in the liquid carried in the supporting portion 114 to relax the muscles of the hands or feet when and to receive stimulation of the magnetic field produced by the magnetic field generator 20.

Figure 8:
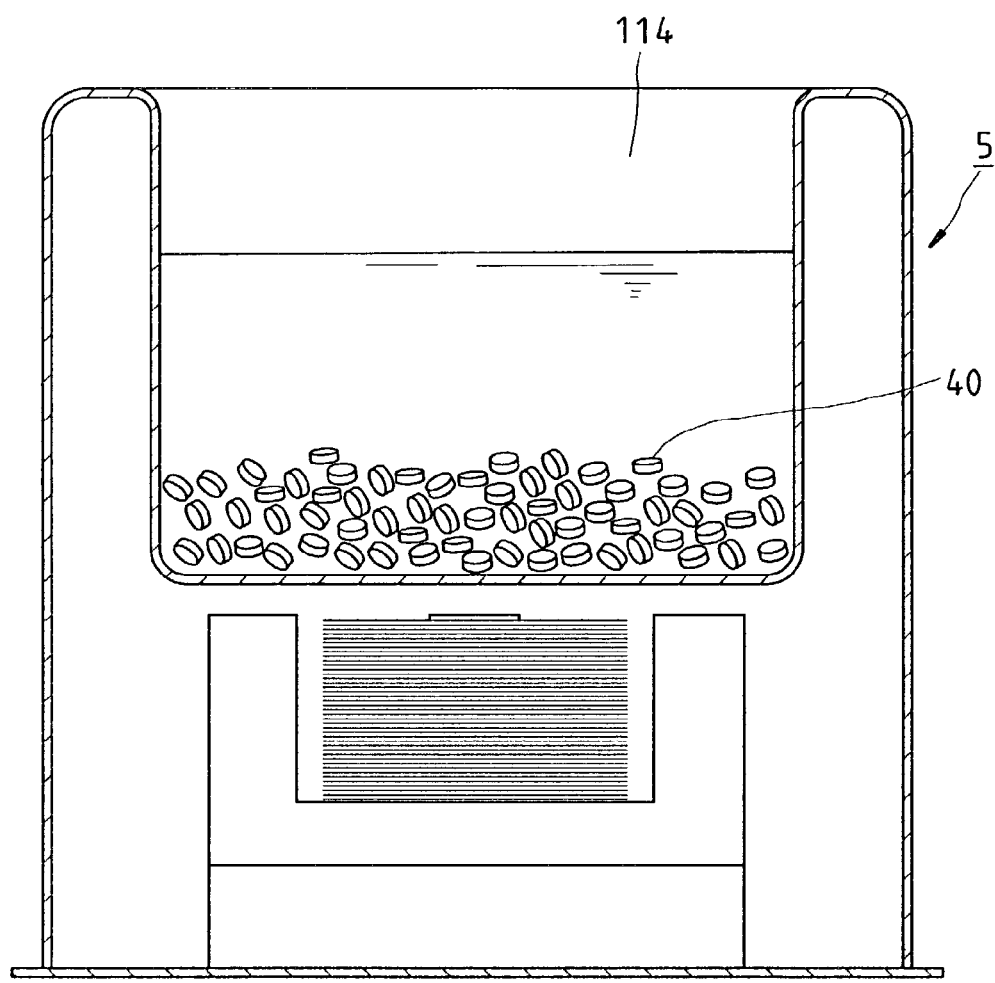
FIG. 8 is similar to FIG. 7 but showing massaging elements put in the liquid in the recessed receiving chamber.
Figure 9:
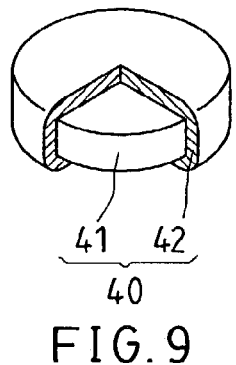
FIG. 9 is a cutaway view of one massaging element according to the fourth embodiment of the present invention.

Referring to FIG. 8, massaging elements 40 may be put in the liquid carried in the recessed receiving chamber (the supporting portion) 114 of the human body massager 5 to produce magnetic attraction/repulsion actions with the magnetic field. Due to magnetic attraction/repulsion actions, the massaging elements 40 are forced to move in the liquid carried in the recessed receiving chamber (supporting portion) 114 and to disturb the liquid, enhancing the massaging effect. The massaging elements 40 can be permanent magnets. As illustrated in FIG. 9, the massaging element 40 is comprised of a magnetic core 41 and a covering 42 holding the magnetic core 41 on the inside. The covering 42 is preferably made of elastic material, for example, rubber, which protects the magnetic core 41 and, improving the bouncing power of the massaging element 40.

Figure 10:
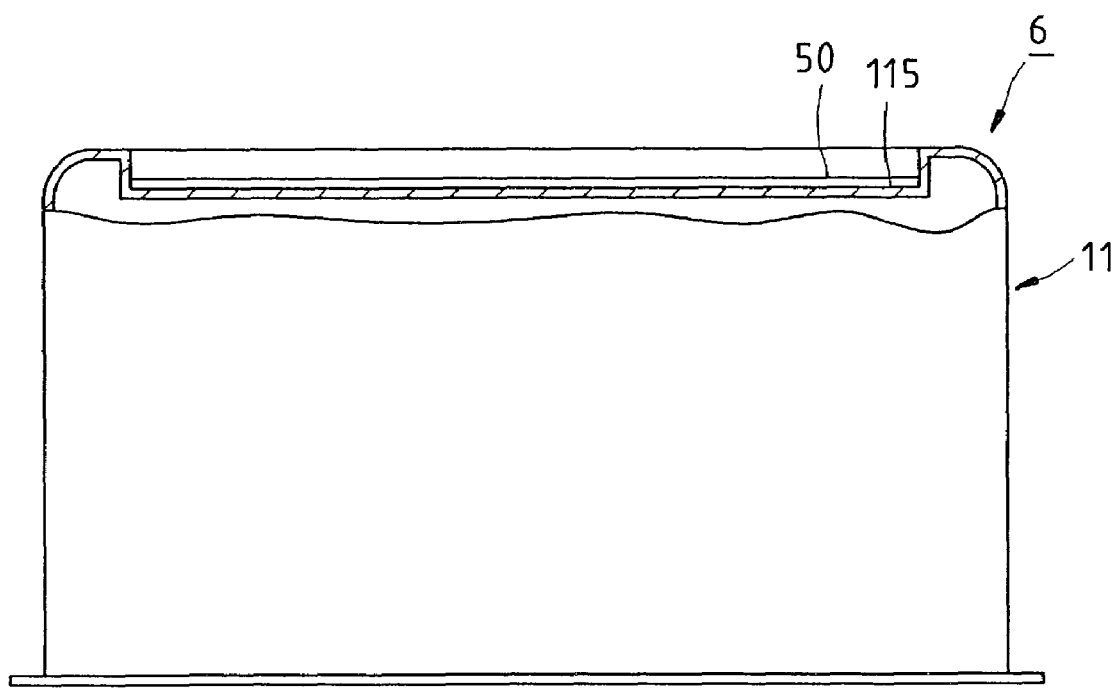
FIG. 10 is a sectional view of a human body massager according to the fifth embodiment of the present invention.

FIG. 10 shows a human body massager 6 according to the fifth embodiment of the present invention. According to this embodiment, the supporting portion (recess) 115 in the top side of the shell 11 of the human body massager 6 is covered with an induction pad 50 made of magnetically conducting metallic material. The induction pad 50 fits the shape of the supporting portion 115. However, the size of the induction pad 50 is relatively smaller than the supporting portion 115. Because the induction pad 50 is made of magnetically conducting metallic material, it produces heat to stimulate the circulation of blood of the user when induced by the magnetic field.

Figure 11:
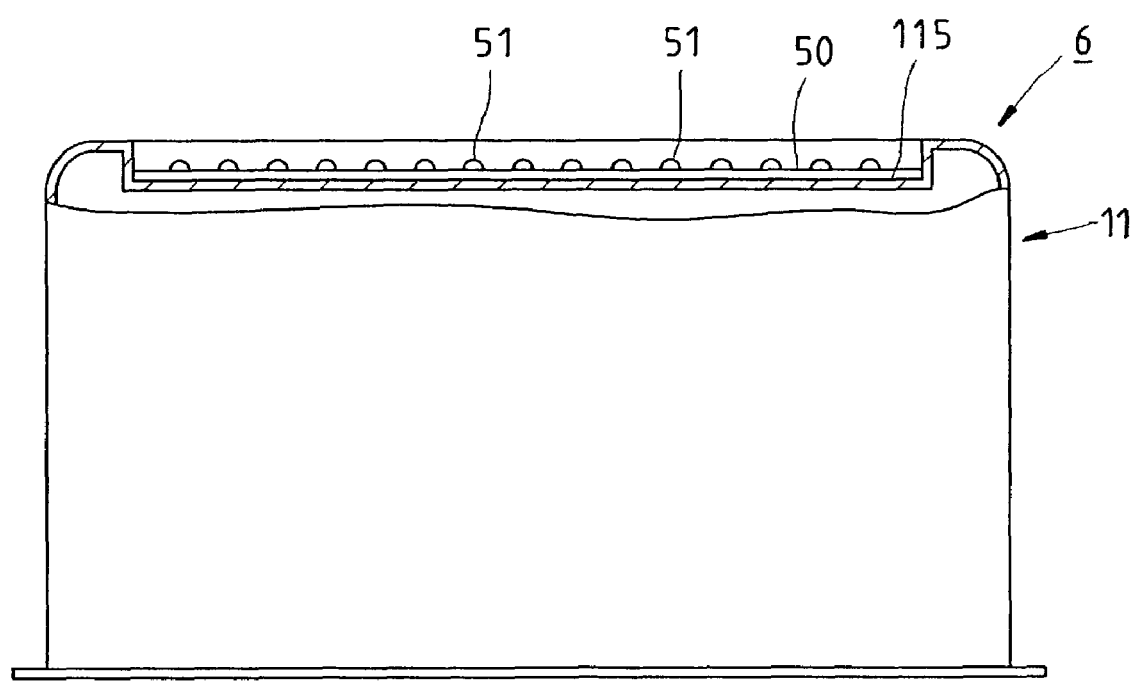
FIG. 11 is an alternate form of the fifth embodiment of the present invention, showing the induction pad provided with raised portions.

Referring to FIG. 11, the induction pad 50 can be made having raised portions 51 for massaging the part of the user's body rested thereon.

Figure 12:
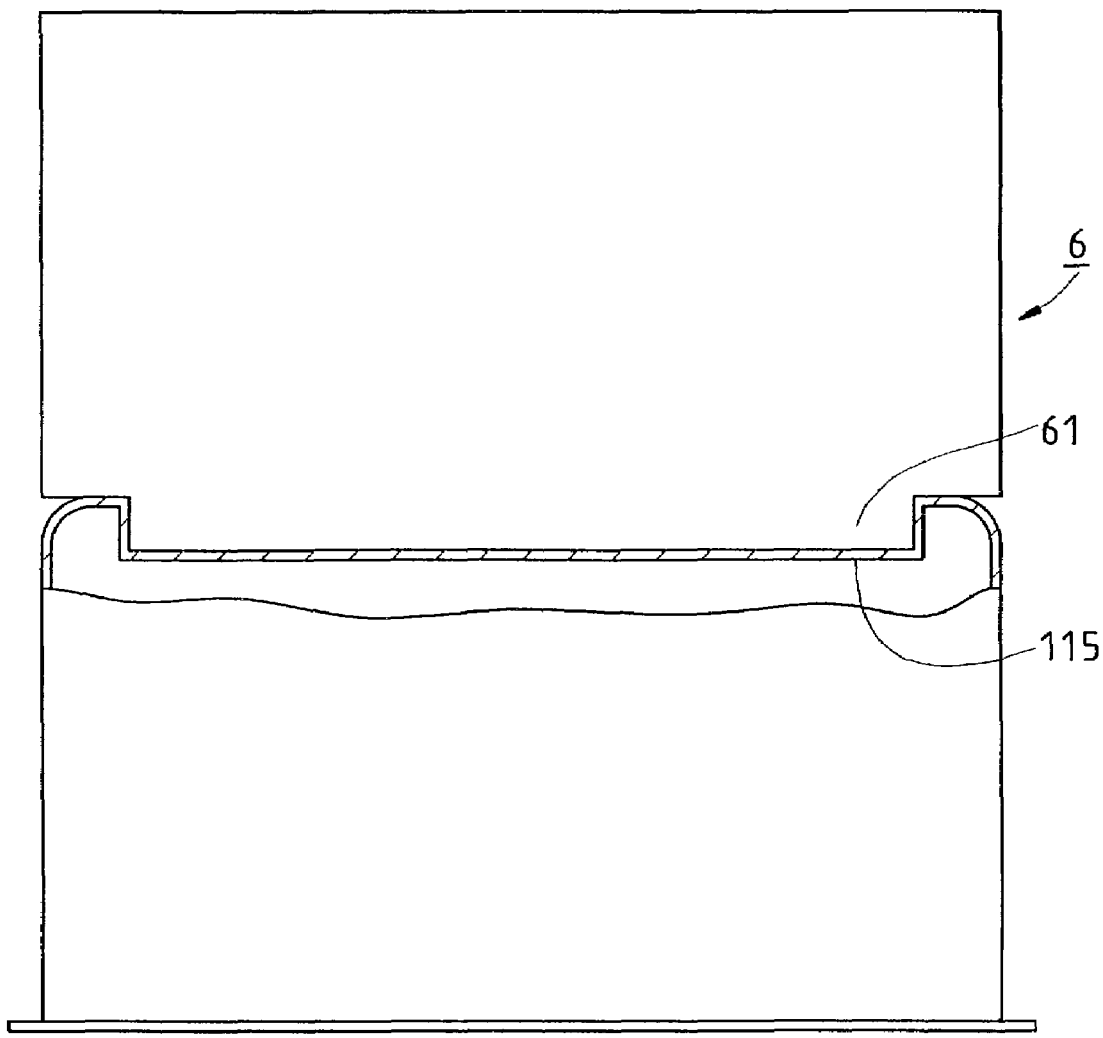
FIG. 12 illustrates a container attached to the supporting portion of the human body massager according to the fifth embodiment of the present invention.

Referring to FIG. 12, a container 60 may be attached to the human body massager 6 to hold a liquid and massaging elements in the liquid like the function of the supporting portion 114 of the embodiment shown in FIG. 4. The container 60 has a bottom positioning flange 61 fitting the recess (supporting portion) 115.

Figure 13:
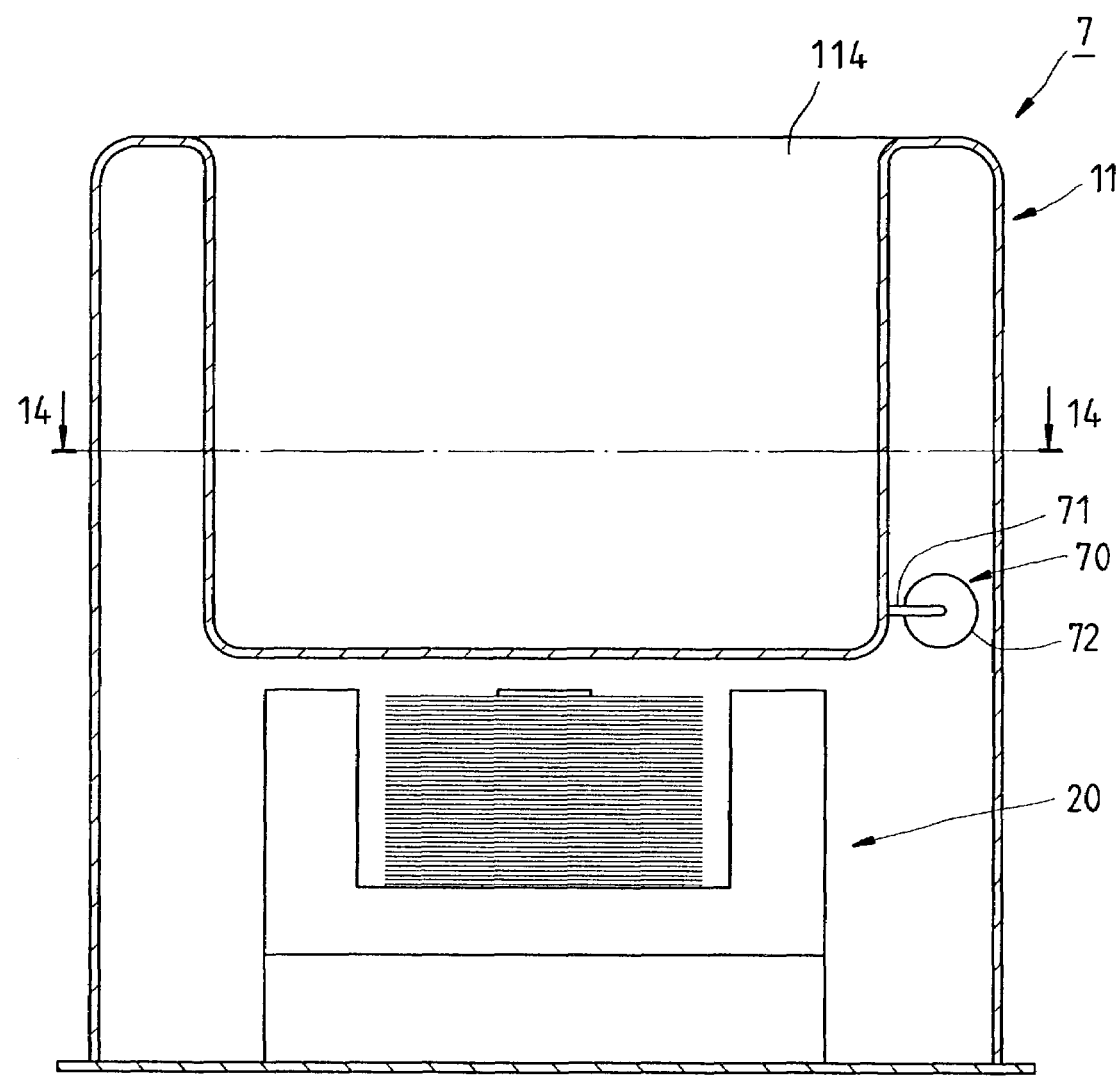
FIG. 13 is a sectional view of a human body massager according to the sixth embodiment of the present invention.
Figure 14:
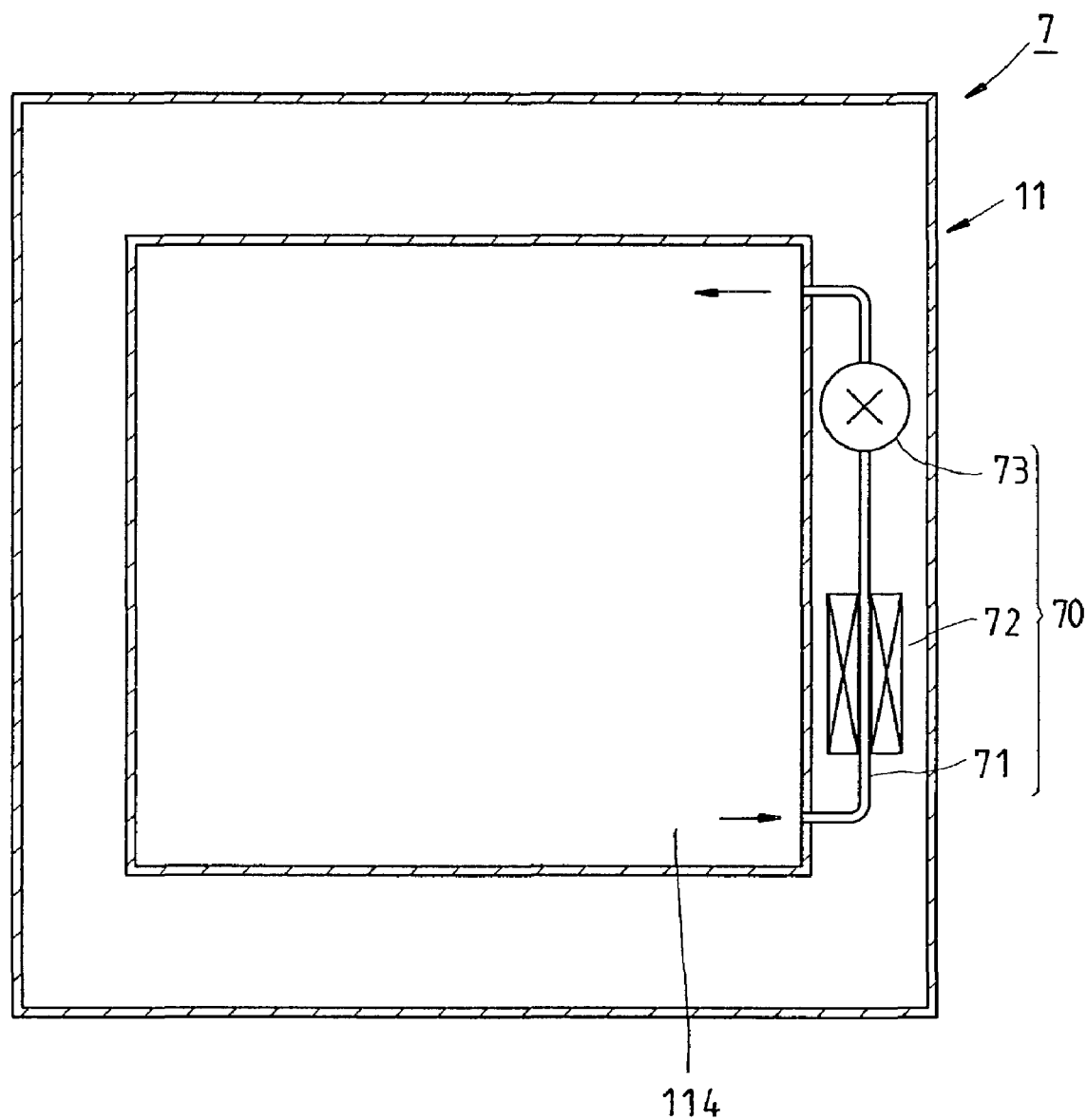
FIG. 14 is a sectional view taken along line 14—14 of FIG. 13.

FIGS. 13 and 14 show a human body massager 7 according to the sixth embodiment of the present invention. This embodiment is similar to the aforesaid fourth embodiment with the exception of the additional water heater 70. The water heater 70 comprises a water passage 71 for circulation of liquid through the recessed receiving chamber (supporting portion) 114, a heating element 72 adapted to heat the liquid passing through the water passage 71, and a pump 73 adapted to pump the liquid, causing the liquid to circulate through the recessed receiving chamber (supporting portion) 114 and the water passage 71. The water heater 70 heats the liquid to the desired temperature level, enhancing the massaging effect of the human body massager 7.

Figure 15:
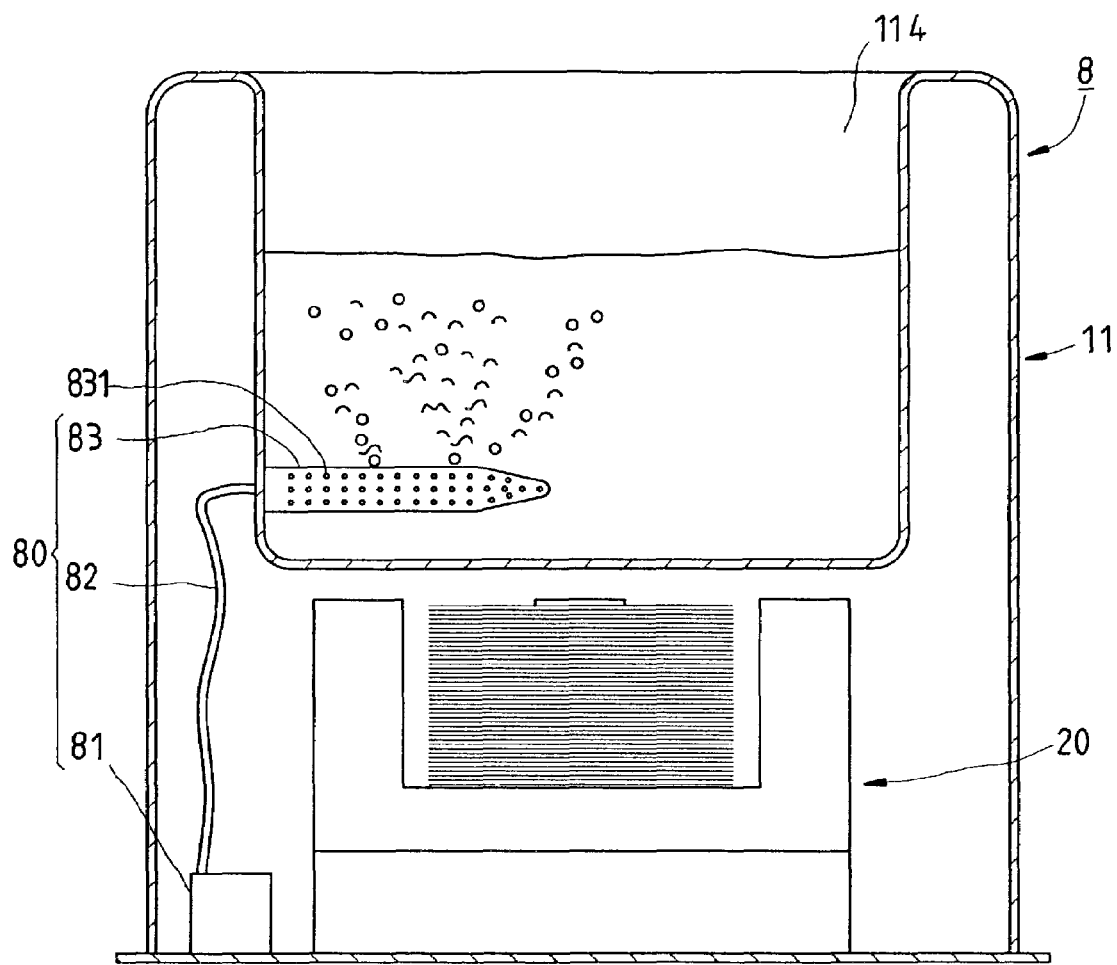
FIG. 15 is a sectional view of a human body massager according to the seventh embodiment of the present invention.

FIG. 15 shows a human body massager 8 according to the seventh embodiment of the present invention. This embodiment is similar to the aforesaid fourth embodiment with the exception of the additional bubble generator 80. The bubble generator 80 comprises an air pump 81 mounted inside the shell 11, a nozzle 83 suspended in the recessed receiving chamber (bearing portion) 114, the nozzle 83 having pores 831, and an air tube 82 connected between the air pump 81 and the nozzle 83. When starting the human body massager 8, the air pump 81 pumps air into the liquid in the recessed receiving chamber (supporting portion) 114 through the air tube 82 and the nozzle 83, thereby causing air bubbles to be produced in the liquid in the recessed receiving chamber (supporting portion) 114.

Figure 16:
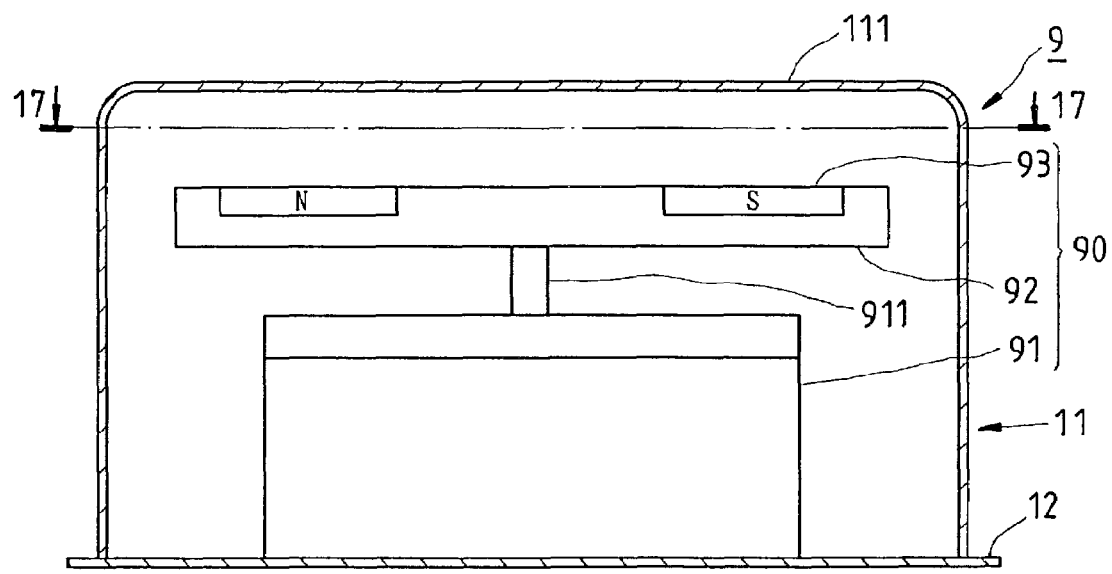
FIG. 16 is a sectional view of a human body massager according to the eighth embodiment of the present invention.
Figure 17:
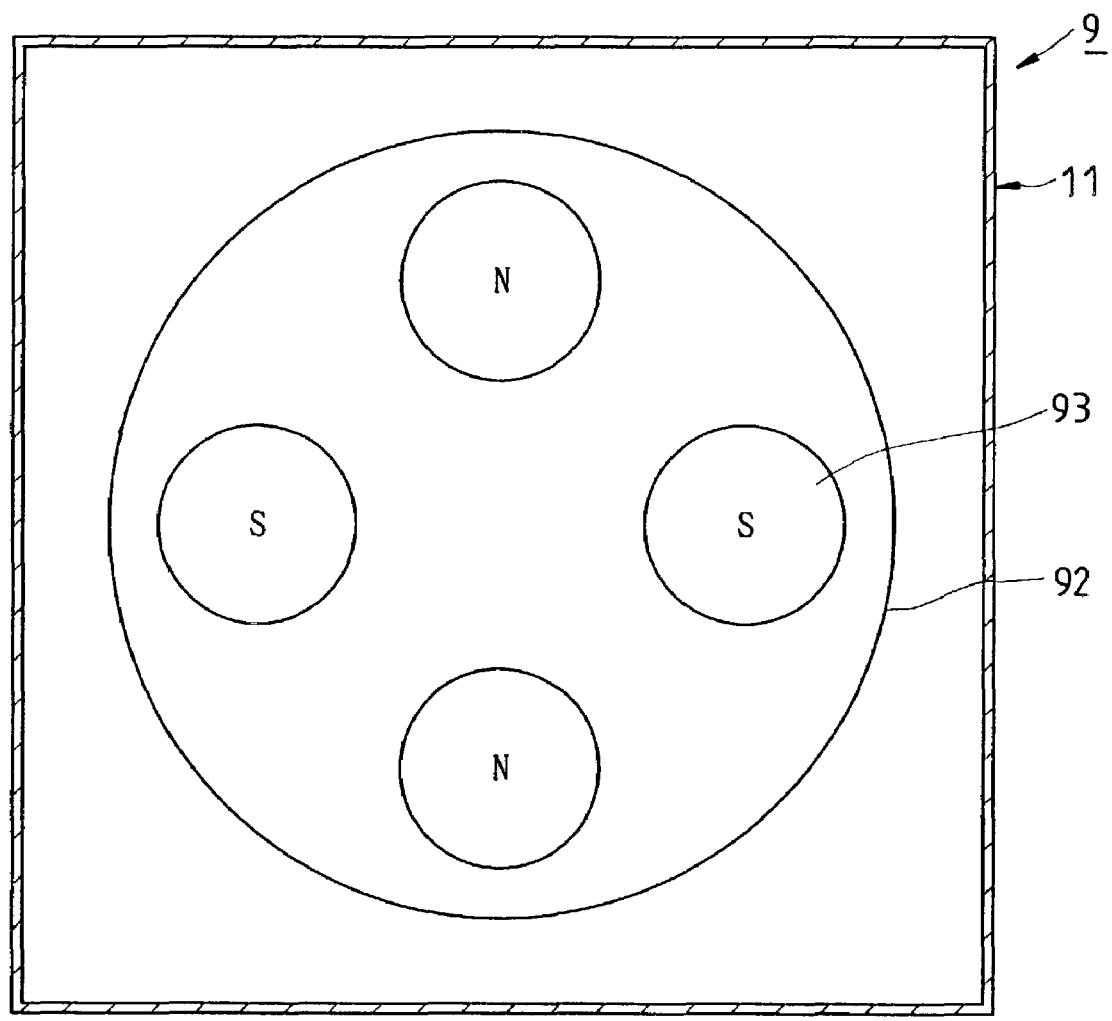
FIG. 17 is a sectional view taken along line 17—17 of FIG. 16.

FIGS. 16 and 17 show a human body massager 9 according to the eighth embodiment of the present invention. This embodiment is similar to the aforesaid first embodiment with the exception of the design of the magnetic field generator 90. The magnetic field generator 90 comprises a motor 91 vertically mounted on the flat cover plate 12, a horizontal wheel 92 fastened to the vertical output shaft 911 of the motor 91, and a plurality of permanent magnets 93 mounted in the horizontal wheel 92 and alternatively reversely arranged around the center of the horizontal wheel 92. The magnetic field inductive range of the permanent magnets 93 covers the whole supporting portion 111. When started the motor 91 to rotate the wheel 92, the permanent magnets 93 are moved with the wheel 92, providing an alternatively varied magnetic field to stimulate the blood circulation of the hand, foot, or hips of the user supporting on the supporting portion 111.

Figure 18:
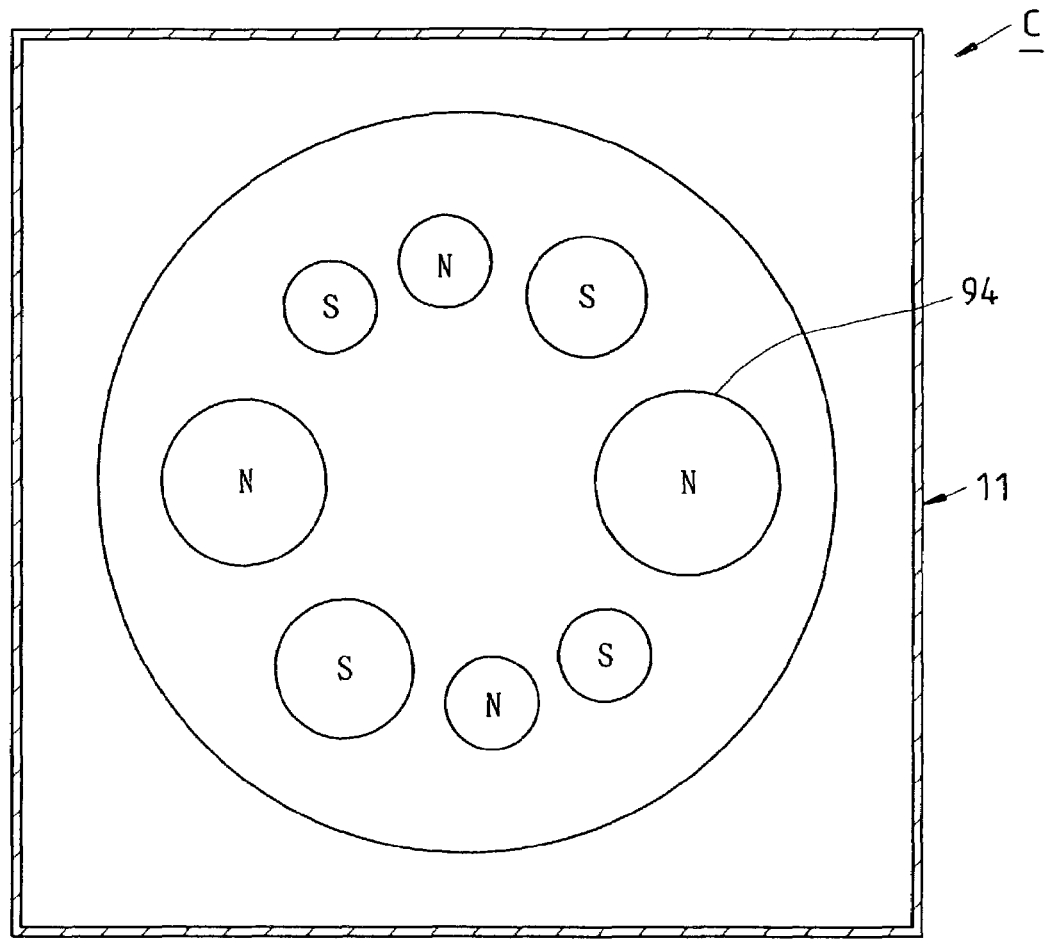
FIG. 18 is a sectional view of a human body massager according to the ninth embodiment of the present invention.

FIG. 18 shows a human body massager C according to the ninth embodiment of the present invention. This embodiment is similar to the aforesaid eighth embodiment with the exception of the arrangement of the permanent magnets. According to this embodiment, the permanent magnets 94 have different magnetic strength. When operated, the permanent magnets 94 provide an intensity and phase alternatively variable magnetic field, enhancing the massaging effect of the human body massager C.

Figure 19:
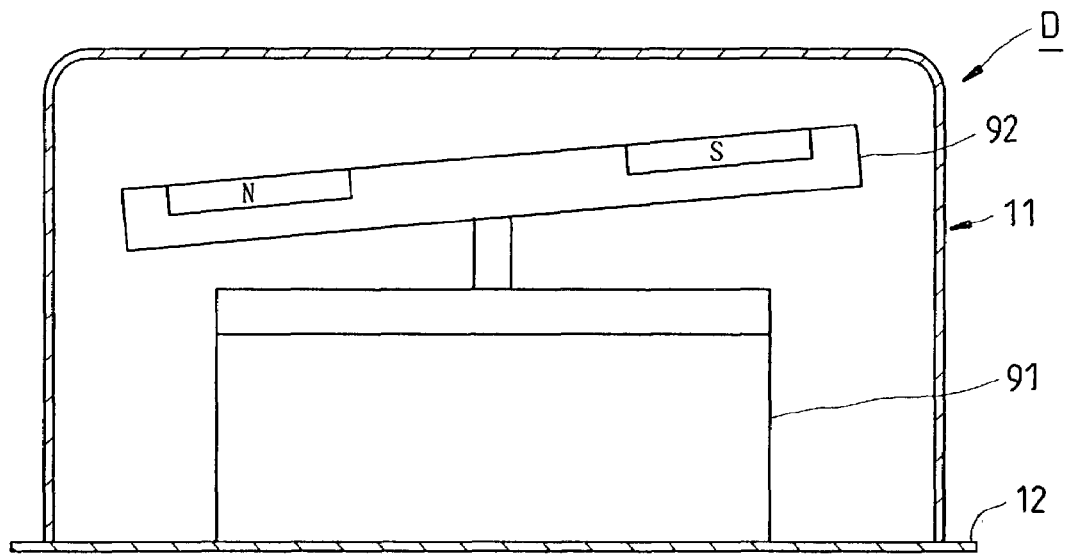
FIG. 19 is a sectional view of a human body massager according to the tenth embodiment of the present invention.

FIG. 19 shows a human body massager D according to the tenth embodiment of the present invention. This embodiment is similar to the aforesaid eighth embodiment. According to this embodiment, the wheel 92 is fixedly fastened to the output shaft of the motor 91 in a sloping position, keeping the permanent magnets 93 spaced from the supporting portion 111 at different distances (see also FIGS. 16 and 17). When operated, the permanent magnets 94 provide an intensity and phase alternatively variable magnetic field, enhancing the massaging effect of the human body massager D.

Figure 20:
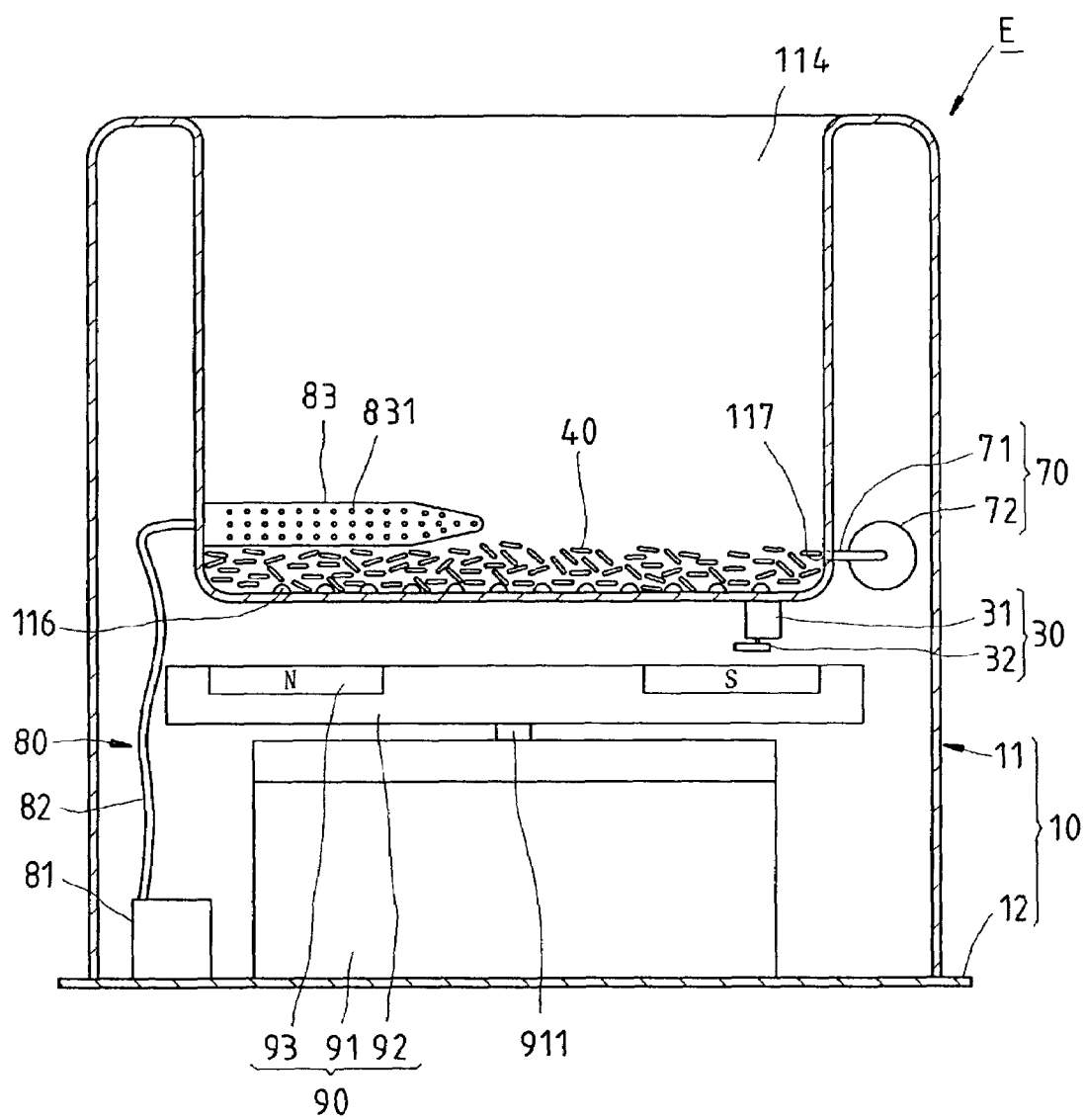
FIG. 20 is a sectional view of a human body massager according to the eleventh embodiment of the present invention.
Figure 21:
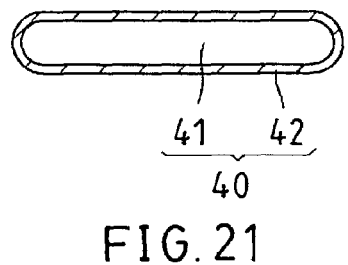
FIG. 21 is a sectional view of one massaging element according to the eleventh embodiment of the present invention.

FIG. 20 shows a human body massager E according to the eleventh embodiment of the present invention. According to this embodiment, the human body massager E comprises a base 10, a vibrator 30, a water heater 70, a bubble generator 80, a magnetic field generator 90, and a plurality of massaging elements 40. The base 10 comprises a hollow shell 11, and a flat a cover plate 12 fixedly fastened to the hollow shell 11 by screws to close the bottom opening of the shell 11. The shell 11 has a recessed receiving chamber (supporting portion) 114 at the top. The recessed receiving chamber (supporting portion) 114 is a recessed receiving chamber for a liquid, having a plurality of raised portions 116 upwardly protruded from the bottom wall thereof and two horizontal through holes 117 disposed in the vertical peripheral wall thereof inside the shell 11. The vibrator 30 comprises a motor 31 mounted in the bottom side of the recessed receiving chamber (supporting portion) 114 inside the shell 11, and an eccentric wheel 32 fastened to the output shaft of the motor 31. The water heater 70 comprises a water passage 71 connected between the through holes 117 of the recessed receiving chamber (supporting portion) 114, a heating element 72 adapted to heat the liquid passing through the water passage 71, and a pump 73 adapted to pump the liquid from the recessed receiving chamber (supporting portion) 114 through the through holes 117 and the water passage 71. The bubble generator 80 comprises an air pump 81 mounted on the cover plate 12 inside the shell 11, a nozzle 83 suspended in the recessed receiving chamber (supporting portion) 114, the nozzle 83 having pores 831, and an air tube 82 connected between the air pump 81 and the nozzle 83. When starting the human body massager E, the air pump 81 pumps air into the liquid in the recessed receiving chamber (supporting portion) 114, producing bubbles. The magnetic generator 90 comprises a motor 91 vertically mounted on the cover plate 12, a wheel 92 fastened to the vertical output shaft 911 of the motor 91, and a plurality of permanent magnets 93 mounted in the horizontal wheel 92 and alternatively reversely arranged around the center of the horizontal wheel 92. The magnetic field inductive range of the permanent magnets 93 covers the recessed receiving chamber (supporting portion) 114. The massaging elements 40 are put in the recessed receiving chamber (supporting portion) 114. As shown in FIG. 21, each massaging element 40 comprises a magnetically conducting core 41 and a covering 42 holding the magnetically conducting core 41 on the inside. The magnetically conducting core 41 can be made of metallic material or permanent magnet. The covering 42 is preferably made of plastics or rubber.

When in use, water, or medical care solution is put in the recessed receiving chamber 114 of the human body massager E, and then the motor 91 is started to rotate the wheel 92, causing the permanent magnets 93 to provide a magnetic field, and then the hands, feet, or any part of the body is dipped in the liquid in the recessed receiving chamber 114. At this time, the massaging elements 40 are forced by the variable magnetic field to hit the part of the user's body in the liquid and to stir up the liquid in the recessed receiving chamber 114, achieving an effective massaging effect. When massaging, the user can turn on the water heater 70, driving the motor 73 to pump the liquid through the water passage 71 and the heating element 72 to heat the liquid passing through the water passage 71. The hot liquid also stimulates the circulation of blood and causes the muscles to relax. The use can also turn on the air pump 81 to pump air through the air tube 82 and the nozzle 83 into the liquid in the recessed receiving chamber 114 to produce bubbles, enhancing the massaging effect. When the user started the motor 31 of the vibrator 30, the eccentric wheel 32 is rotated to vibrate the bottom wall of the recessed receiving chamber 114, causing the raised portions 116 to rub the contact part of the user's body.

In actual practice, the human body massager E can be equipped with a microprocessor for controlling the revolving speed of the motor 91 of the magnetic field generator 90, the heating temperature of the water heater 70, and the pumping speed of the air pump 81 of the bubble generator 80.

A prototype of human body massager has been constructed with the features of FIGS. 1~21. The human body massager functions smoothly to provide all of the features discussed earlier.

Although particular embodiments of the invention have been described in detail for purposes of illustration, various modifications and enhancements may be made without departing from the spirit and scope of the invention. Accordingly, the invention is not to be limited except as by the appended claims.

What the invention claimed is:
1. A human body massager comprising:
   a base having a supporting portion for supporting a human body; and a magnetic field generator installed in said base and adapted for generating a variable magnetic field involved with the human body, wherein said magnetic field generator comprises a motor installed in said base, said motor having an output shaft aimed at said supporting portion, a wheel mounted on the output shaft of said motor for synchronous rotation with the output shaft of said motor, and a plurality of permanent magnets alternatively reversely arranged around the center of said wheel and having different magnetic strength;

wherein the magnetic field inductive range of said permanent magnets covers said supporting portion.

2. The human body massager as claimed in claim 1, wherein said wheel is perpendicularly fastened to the output shaft of said motor.

3. The human body massager as claimed in claim 1, wherein said wheel is fastened to the output shaft of said motor in a sloping position.

4. A human body massager comprising:
a base having a supporting portion for supporting a human body; and
a magnetic field generator installed in said base and adapted for generating a variable magnetic field involved with the human body, wherein said magnetic field generator comprises a motor installed in said base, said motor having an output shaft aimed at said supporting portion, a wheel mounted on the output shaft of said motor for synchronous rotation with the output shaft of said motor, and a plurality of permanent magnets alternatively reversely arranged around the center of said wheel, wherein said wheel is fastened to the output shaft of said motor in a sloping position; and
wherein the magnetic field inductive range of said permanent magnets covers said supporting portion.

5. The human body massager as claimed in claim 4, wherein said permanent magnets have different strength.

6. The human body massager as claimed in claim 1 or 4, wherein said variable magnetic field changes the intensity with time.

7. The human body massager as claimed in claim 1 or 4, wherein said variable magnetic field changes the phase with time.

8. The human body massager as claimed in claim 1 or 4, wherein said supporting portion is a platform adapted for carrying a part of the users body such as the hands, the legs, or the hips.

9. The human body massager as claimed in claim 1 or 4, wherein said supporting portion is a recessed member fitting a part of the human body.

10. The human body massager as claimed in claim 1 or 4, wherein said supporting portion has raised portions protruded from a top side thereof for massaging a part of the user's body.

11. The human body massager as claimed in claim 10, further comprising a vibrator installed in said base and adapted to vibrate said supporting portion.

12. The human body massager as claimed in claim 11, wherein said vibrator comprises a motor having an output shaft and an eccentric wheel fastened to the output shaft of the motor.

13. The human body massager as claimed in claim 1 or 4, wherein said supporting portion is a recessed receiving chamber adapted for carrying a liquid.

14. The human body massager as claimed in claim 13 further comprising a plurality of magnetic massaging elements put in said recessed receiving chamber.

15. The human body massager as claimed in claim 14, wherein said magnetic massaging elements are permanent magnets.

16. The human body massager as claimed in claim 15, further comprising a plurality of massaging elements put in said recessed receiving chamber, said massaging elements each comprising a magnetic core and a covering that covers said magnetic core.

17. The human body massager as claimed in claim 16, wherein said covering is made of rubber.

18. The human body massager as claimed in claim 13, wherein said recessed receiving chamber comprises a plurality of raised portions upwardly protruded from a bottom wall thereof.

19. The human body massager as claimed in claim 13, further comprising a water heater, said water heater comprising a water passage for circulation of the liquid carried in said recessed receiving chamber, a pump adapted to pump the liquid from said recessed receiving chamber through said water passage and into said recessed receiving chamber again, and an electric heating element adapted to heat the liquid passing through said recessed receiving chamber.

20. The human body massager as claimed in claim 13, further comprising a bubble generator, said bubble generator comprising an air pump, a nozzle suspended in said recessed receiving chamber, and an air tube connected between said air pump and said nozzle for guiding air from said air pump into the liquid carried in said recessed receiving chamber through said nozzle for producing bubbles.

21. The human body massager as claimed in claim 1 or 4, further comprising an induction pad;
wherein said supporting portion is a recessed member fitting a part of the human body; and
wherein said induction pad is made of magnetically inducting metallic material and is placed on a top surface of said recessed member, said induction pad having a shape fitting said top surface of said recessed member and a size smaller than said top surface.

22. The human body massager as claimed in claim 21, wherein said induction pad comprises a plurality of raised portions upwardly protruded from a top surface thereof.

23. The human body massager as claimed in claim 1 or 4, wherein said supporting portion comprises a top recess and a water container mountable to said top recess, said water container having a bottom coupling flange fitting said top recess.

24. The human body massager as claimed in claim 1 or 4, wherein said base comprises a hollow shell injection-molded from plastics, said hollow shell having a top side forming said supporting portion and a bottom open side, and a cover plate covered on said bottom open side of said hollow shell to hold said magnetic field generator inside said shell.

* * * * *